US010517531B2

(12) United States Patent
Vardas

(10) Patent No.: US 10,517,531 B2
(45) Date of Patent: Dec. 31, 2019

(54) STRESS MANAGEMENT USING BIOFEEDBACK

(71) Applicant: Vardas Inc., El Dorado Hills, CA (US)

(72) Inventor: Chad Vardas, El Dorado Hills, CA (US)

(73) Assignee: Vardas Solutions LLC, El Dorado Hills, CA (US)

( * ) Notice: Subject to any disclaimer, the term of this patent is extended or adjusted under 35 U.S.C. 154(b) by 16 days.

(21) Appl. No.: 15/428,115

(22) Filed: Feb. 8, 2017

(65) Prior Publication Data

US 2017/0224273 A1    Aug. 10, 2017

Related U.S. Application Data

(60) Provisional application No. 62/292,450, filed on Feb. 8, 2016.

(51) Int. Cl.
*A61B 5/024*    (2006.01)
*A61B 5/00*    (2006.01)

(52) U.S. Cl.
CPC .......... *A61B 5/486* (2013.01); *A61B 5/02405* (2013.01); *A61B 5/02438* (2013.01); *A61B 5/6824* (2013.01); *A61B 5/742* (2013.01); *A61B 5/7455* (2013.01)

(58) Field of Classification Search
CPC .......... A61B 5/02405; A61B 5/150816; A61B 5/486; A61B 5/6802; A61B 5/681; A61B 5/7455
See application file for complete search history.

(56) References Cited

U.S. PATENT DOCUMENTS

| | | | |
|---|---|---|---|
| 5,682,898 A | 11/1997 | Kung et al. |
| 6,212,427 B1 | 4/2001 | Hoover et al. |
| 6,305,943 B1 | 10/2001 | Pougatchev et al. |
| 6,358,201 B1 | 3/2002 | Childre et al. |
| 6,377,845 B1 | 4/2002 | Kinast |
| 6,656,116 B2 | 12/2003 | Kim et al. |
| 6,836,681 B2 | 12/2004 | Stabler et al. |
| 7,117,032 B2 | 10/2006 | Childre et al. |
| 7,163,512 B1 | 1/2007 | Childre et al. |
| D554,266 S | 10/2007 | Striepe et al. |

(Continued)

FOREIGN PATENT DOCUMENTS

| | | |
|---|---|---|
| CN | 103690166 A | 4/2014 |
| WO | 200028892 A1 | 5/2000 |

(Continued)

OTHER PUBLICATIONS

Love your heart every day, Jan. 29, 2016, http://www.alivecor.com:80/home, Retrieved Jul. 31, 2018, pp. 1-3.

(Continued)

*Primary Examiner* — Allen Porter
(74) *Attorney, Agent, or Firm* — Dergosits & Noah LLP

(57) ABSTRACT

A wearable device or apparatus is used for monitoring biometric data of a user and enabling biofeedback indications in response to biometric data received. In one embodiment, the wearable device includes at least one sensor, a button, at least one processor having a memory unit coupled to the at least one sensor and a feedback mechanism. The feedback mechanism can include a biofeedback indicator.

16 Claims, 5 Drawing Sheets

(56) References Cited

U.S. PATENT DOCUMENTS

| | | | |
|---|---|---|---|
| 7,462,151 | B2 | 12/2008 | Childre et al. |
| 7,618,378 | B2 | 11/2009 | Bingham et al. |
| 7,691,049 | B2 | 4/2010 | Wood et al. |
| 8,066,637 | B2 | 1/2011 | Childre et al. |
| 8,002,711 | B2 | 8/2011 | Wood et al. |
| 8,123,696 | B2 | 2/2012 | Childre et al. |
| 8,301,232 | B2 | 10/2012 | Albert et al. |
| 8,306,621 | B2 | 11/2012 | Kim et al. |
| 8,509,882 | B2 | 8/2013 | Albert et al. |
| 8,523,758 | B1 | 9/2013 | Kirby et al. |
| 8,543,197 | B2 | 9/2013 | Striepe et al. |
| 8,700,137 | B2 | 4/2014 | Albert |
| 8,764,673 | B2 | 7/2014 | McCraty et al. |
| 8,936,556 | B2 | 1/2015 | Lee et al. |
| 8,938,288 | B2 | 1/2015 | Wood et al. |
| 9,026,202 | B2 | 5/2015 | Albert |
| 9,113,612 | B2 | 8/2015 | Koyrakh et al. |
| 9,220,430 | B2 | 12/2015 | Albert |
| 9,247,911 | B2 | 2/2016 | Galloway et al. |
| 9,254,092 | B2 | 2/2016 | Albert et al. |
| 9,254,095 | B2 | 2/2016 | Galloway et al. |
| 9,351,654 | B2 | 5/2016 | Albert |
| 9,420,956 | B2 | 8/2016 | Gopalakrishnan et al. |
| 9,572,499 | B2 | 2/2017 | Gopalakrishnan et al. |
| 9,579,062 | B2 | 2/2017 | Albert |
| 9,610,017 | B2 | 4/2017 | Casal et al. |
| 9,699,528 | B2 | 7/2017 | Dixit et al. |
| 9,830,832 | B2 | 11/2017 | Warren et al. |
| 9,913,612 | B2 | 3/2018 | Banet et al. |
| 2005/0033189 | A1 | 2/2005 | McCraty et al. |
| 2005/0124906 | A1 | 6/2005 | Childre et al. |
| 2005/0209504 | A1 | 9/2005 | Elliott et al. |
| 2005/0288601 | A1 | 12/2005 | Wood et al. |
| 2007/0021675 | A1 | 1/2007 | Childre et al. |
| 2007/0270668 | A1 | 11/2007 | Childre et al. |
| 2007/0299354 | A1 | 12/2007 | Striepe et al. |
| 2008/0035147 | A1 | 2/2008 | Kirby et al. |
| 2008/0319513 | A1 | 12/2008 | Pu et al. |
| 2009/0137915 | A1 | 5/2009 | Childre et al. |
| 2009/0192541 | A1* | 7/2009 | Ortiz .................. A61F 5/0059 606/192 |
| 2009/0281400 | A1 | 11/2009 | McCraty et al. |
| 2010/0041967 | A1 | 2/2010 | McCraty et al. |
| 2010/0174205 | A1* | 7/2010 | Wegerif ............. A61B 5/02405 600/515 |
| 2011/0004047 | A1 | 1/2011 | Braspenning et al. |
| 2011/0301435 | A1 | 2/2011 | Albert et al. |
| 2011/0301439 | A1 | 12/2011 | Albert et al. |
| 2012/0172689 | A1 | 7/2012 | Albert et al. |
| 2013/0197320 | A1 | 8/2013 | Albert et al. |
| 2014/0050321 | A1 | 2/2014 | Albert et al. |
| 2014/0066798 | A1 | 3/2014 | Albert |
| 2014/0128758 | A1 | 5/2014 | Galloway et al. |
| 2014/0194760 | A1 | 7/2014 | Albert |
| 2014/0221859 | A1 | 8/2014 | Albert |
| 2014/0228665 | A1 | 8/2014 | Albert |
| 2014/0276162 | A1 | 9/2014 | Albert et al. |
| 2015/0018660 | A1 | 1/2015 | Thomson et al. |
| 2015/0018702 | A1 | 1/2015 | Galloway et al. |
| 2015/0045641 | A1* | 2/2015 | Rule .................. A61B 5/7435 600/347 |
| 2015/0073285 | A1 | 3/2015 | Albert et al. |
| 2015/0087952 | A1 | 3/2015 | Albert et al. |
| 2015/0164349 | A1 | 6/2015 | Gopalakrishnan et al. |
| 2015/0238147 | A1 | 8/2015 | Figgatt et al. |
| 2015/0265164 | A1 | 9/2015 | Gopalakrishnan et al. |
| 2015/0297134 | A1 | 10/2015 | Albert et al. |
| 2015/0317885 | A1 | 11/2015 | Ramstein et al. |
| 2015/0320328 | A1 | 11/2015 | Albert |
| 2016/0038083 | A1* | 2/2016 | Ding .................. A61B 5/6804 600/388 |
| 2016/0074674 | A1 | 3/2016 | Kohli et al. |
| 2016/0184518 | A1 | 6/2016 | Freeman et al. |
| 2016/0234572 | A1 | 8/2016 | Dixit |
| 2016/0235319 | A1 | 8/2016 | Albert |
| 2016/0242665 | A1 | 8/2016 | Galloway et al. |
| 2016/0242697 | A1 | 8/2016 | Albert |
| 2016/0249823 | A1 | 9/2016 | Galloway et al. |
| 2016/0331247 | A1 | 11/2016 | Albert |
| 2016/0367157 | A1* | 12/2016 | Blake .................. A61B 5/02405 |
| 2017/0011210 | A1 | 1/2017 | Cheong et al. |
| 2017/0325700 | A1 | 11/2017 | Lane et al. |
| 2018/0014778 | A1* | 1/2018 | Cronin .................. A61B 5/681 |
| 2018/0312167 | A1 | 11/2018 | Kundu |

FOREIGN PATENT DOCUMENTS

| | | |
|---|---|---|
| WO | 2000051677 A2 | 9/2000 |
| WO | 2005015157 A2 | 2/2005 |
| WO | 2005044092 A2 | 5/2005 |
| WO | 2010014170 A1 | 2/2010 |
| WO | 2011156374 A2 | 12/2011 |
| WO | 2012158190 A1 | 11/2012 |
| WO | 2013112979 A1 | 8/2013 |
| WO | 2014028899 A1 | 2/2014 |
| WO | 2014036436 A1 | 3/2014 |
| WO | 2014074913 A1 | 5/2014 |
| WO | 2014107700 A1 | 7/2014 |
| WO | 2014145927 A1 | 9/2014 |
| WO | 2014172451 A1 | 10/2014 |
| WO | 2015035251 A1 | 3/2015 |
| WO | 2015089484 A1 | 6/2015 |
| WO | 2015164404 A1 | 10/2015 |
| WO | 2015171764 A1 | 11/2015 |
| WO | 2016183515 A1 | 11/2016 |

OTHER PUBLICATIONS

To wear it is to love it., Feb. 7, 2016, https://www.apple.com/watch/, Retrieved Jun. 28, 2018, pp. 1-9.
A smarter way to look at health and fitness, Feb. 1, 2016, http://www.apple.com/watch/health-and-fitness/, Retrieved Jun. 28, 2018, pp. 1-13.
A smarter way to look at health and fitness, Jan. 15, 2016, www.apple.com/watch/health-and-fitness, Retrieved Jun. 29, 2018, pp. 1-9.
Introducing Sona Connected Bracelet for Mind and Body, Jan. 23, 2016, http://www.caeden.com/collectons/sona/, Retrieved Jul. 31, 2018, pp. 1-8.
Every beat counts, Feb. 6, 2016, https://www.fitbit.com/chargehr, Retrieved Jul. 26, 2018, pp. 1-10.
Introducing fitbit alta, Fitness Wristband, Feb. 6, 2016, https://fitbit.com//home, Retrieved Jul. 26, 2018, pp. 1-2.
Summary of buy.garmin.com, 2016, https://buygarmin.com/en-US/US-wearabletech/wearables/c1001-c1002-p1, Retrieved Jul. 31, 2018, pp. 1-2.
Measure. Revitalize. Repeat., Feb. 5, 2016, https://store.heartmath.com, Retrieved Jul. 26, 2018, pp. 1-4.
EmWave2, What can you achieve? Jan. 3, 2016, http://store.heartmath.com/emwave2, Retrieved Jul. 26, 2018, pp. 1-5.
EmWave Pro, Help your clients achieve more meaningful results, http://store.heartmath.com/emwavepro, Jan. 3, 2016, Retrieved Jul. 26, 2018, pp. 1-5.
HeHa's mission is to bring "cool" to everyone and help others to live healthy and happy, http://www.iheha.com:80hk-tc/index.html, Retrieved Jul. 31, 2018, pp. 1-3.
Muse is your personal meditation assistant, Feb. 6, 2016, https://www.chosemuse.com, Retrieved Jul. 26, 2018, pp. 1-4.
Prana aims to change how you behave, Jan. 10, 2016, https://prana.co, Retrieved Jul. 31, 2018, pp. 1-10.
My first week with Spire was the most calm I've had in ten years, Feb. 6, 2016, https://spire.io, Retrieved Jul. 26, 2018, pp. 1-6.
Shift beyond chemicals to achieve peak performance, Feb. 5, 2016, http://www.thync.com/, Retrieved Jul. 31, 2018, pp. 1-5.
International Search Report and Written Opinion, PCT/US17/17065, dated May 16, 2017, 22 pages.
Google translation of CN103211603, Jul. 24, 2013, Mental stress detecting,tracking and feedback system, chrome-extension://nlipoenfbbikpbjkfpfillcgkoblgpmj/edit.html, retrieved Jan. 30, 2019, 4 pages.

(56) References Cited

OTHER PUBLICATIONS

Jia et al., "Monitoring a Person's Heart Rate and Respiratory Rate on a Shared Bed Using Geophones," In. Proceedings of the 15th ACM Conference on Embedded Network Sensor Systems, Nov. 6, 2017, Retrieved from http://www.winlab.rutgers.edu/-sugangli/papers/Sensys_2017.pdf, 16 pages.
Notification of Transmittal of the International Search Report and the Written Opinion of the International Searching Authority, International Application No. PCT/US2018/037156, dated Sep. 21, 2018, 22 pages.
Pan et al., "A Real-Time QRS Detection Algorithm," IEEE Transactions on Biomedical Engineering, vol. BME-32, No. 3, Mar. 1985, pp. 230-236.
Trobec et al., "Two Proximal Skin Electrodes—A Respiration Rate Body Sensor," Sensors, 2012, 12, pp. 13813-13828.
Amit K. Gupta, "Respiration Rate Measurement Based on Impedence Pneumography," Texas Instruments, Application Report, SBAA181—Feb. 2011, 11 pages.
ADS1291, ADS1292, ADS1292R, Texas Instruments, SBAS502B, Dec. 2011—Revised Sep. 2012, p. 12 and pp. 56-60.
Google translation of CN103690166, Apr. 2, 2014, One kind of three-dimensional electrical impedance imaging system and the imaging method based on the bus during breathing pxl, chrome-extension://nlipoenfbbikpbjkfpfillcgkoblgpmj/edit.html, retrieved Feb. 27, 2019 pp. 4.

\* cited by examiner

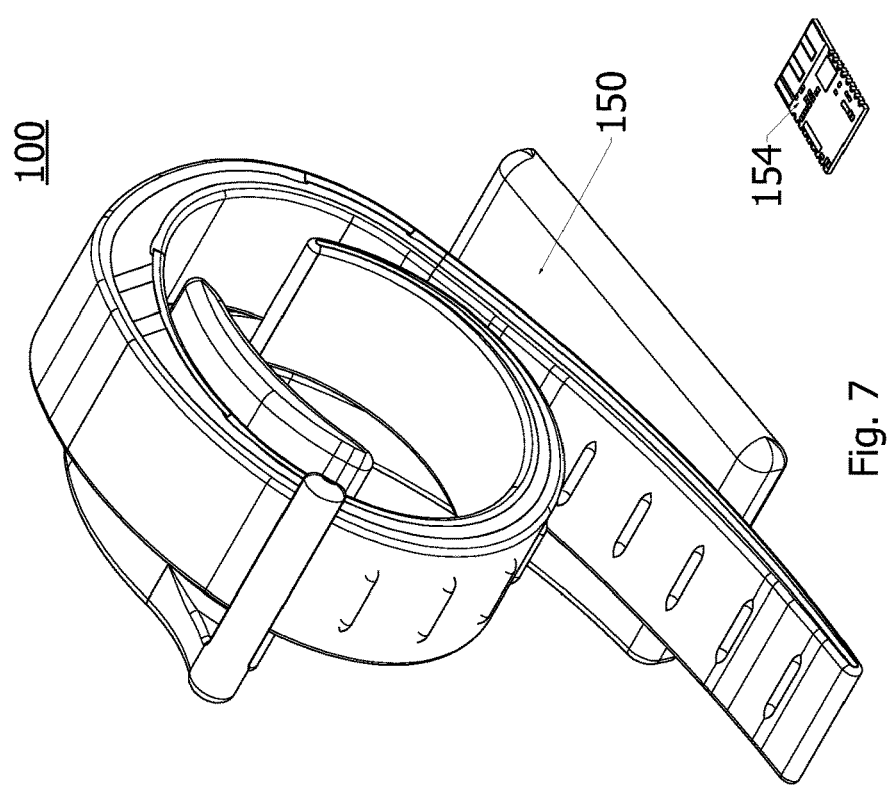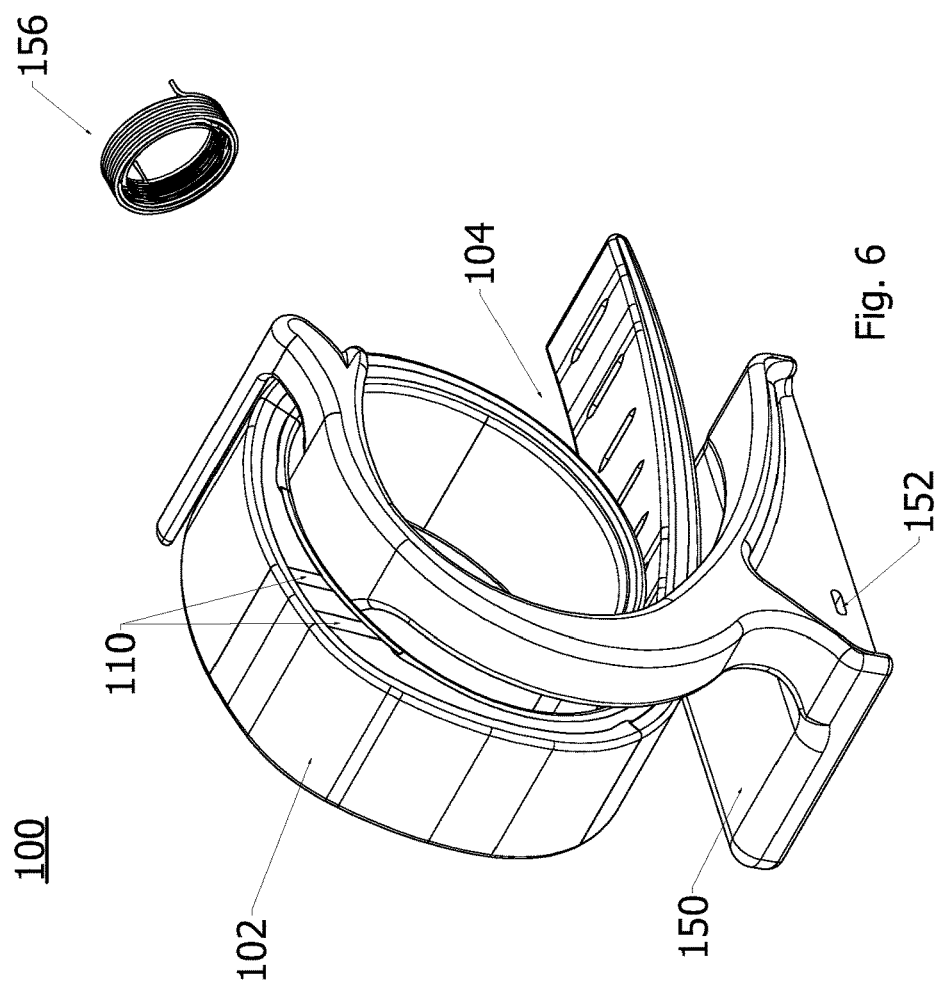

STRESS MANAGEMENT USING BIOFEEDBACK

CROSS REFERENCE TO RELATED APPLICATIONS

This application claims the benefit of U.S. provisional patent application No. 62/292,450, filed on Feb. 8, 2016, which is incorporated herein by reference in its entirety.

BACKGROUND

Current biometric monitoring devices make information about bodily processes available to a user through one of the user's senses, in some cases allowing the user to interpret the information and alter his/her activity in order to attain the desired bodily process measurements. These biometric monitoring devices may collect, derive, and provide one or more of the following types of information: heart rate, sweat content, calorie burn, ambulatory speed and/or distance traveled etc. Monitoring a person's physiological characteristics can be used to provide biofeedback about one's physiological state. For example, portable heart rate monitors and other monitoring devices currently include blinking lights or notification sounds or vibrations to alert the user to a particular parameter or end point.

SUMMARY

Concepts presented herein relate to a wearable device or apparatus for monitoring biometric data of a user and enabling biofeedback indications in response to biometric data received. In one embodiment, the wearable device includes at least one sensor, a button, at least one processor having a memory unit coupled to the at least one sensor and a feedback mechanism. The feedback mechanism can include a biofeedback indicator.

In one particular aspect, a system is described that includes a biometric monitoring device and a heart rate variability measuring function. The system may include: at least one sensor, a button to provide an activation signal to the sensor when a user actuates the button, at least one processor and memory. In this implementation, the sensor, the button, the at least one processor and the memory are communicatively connected. Further, the memory stores computer-executable instructions for controlling the at least one processor to cause the sensor to start collecting data in response to the activation signal from the button. Furthermore, the device is configured to provide user feedback, through a feedback mechanism, with reference to the collected data. The feedback mechanism further comprises a vibrator as a biofeedback indicator and the feedback to the user is provided as haptic vibration.

These and other advantages and features of the concepts presented herein are described with specificity so as to make the present disclosure understandable to one of ordinary skill in the art.

BRIEF DESCRIPTION OF THE DRAWINGS

FIG. 6 is a perspective view of the biometric monitoring device of FIG. 2 positioned on a charging stand.

FIG. 7 is another perspective view of the biometric monitoring device of FIG. 2 positioned on a charging stand.

DETAILED DESCRIPTION OF THE DRAWINGS

In the following discussion that addresses a number of embodiments, reference is made to the accompanying drawings that form a part hereof, and in which is shown by way of illustration of specific embodiments. It is to be understood that other embodiments may be utilized and changes may be made without departing from the scope of the concepts presented herein.

Various inventive features are described below that can each be used independently of one another or in combination with other features. However, any single inventive feature may not address any of the problems discussed above or only address one of the problems discussed above. Further, one or more of the problems discussed above may not be fully addressed by any of the features described below.

Figure 1:
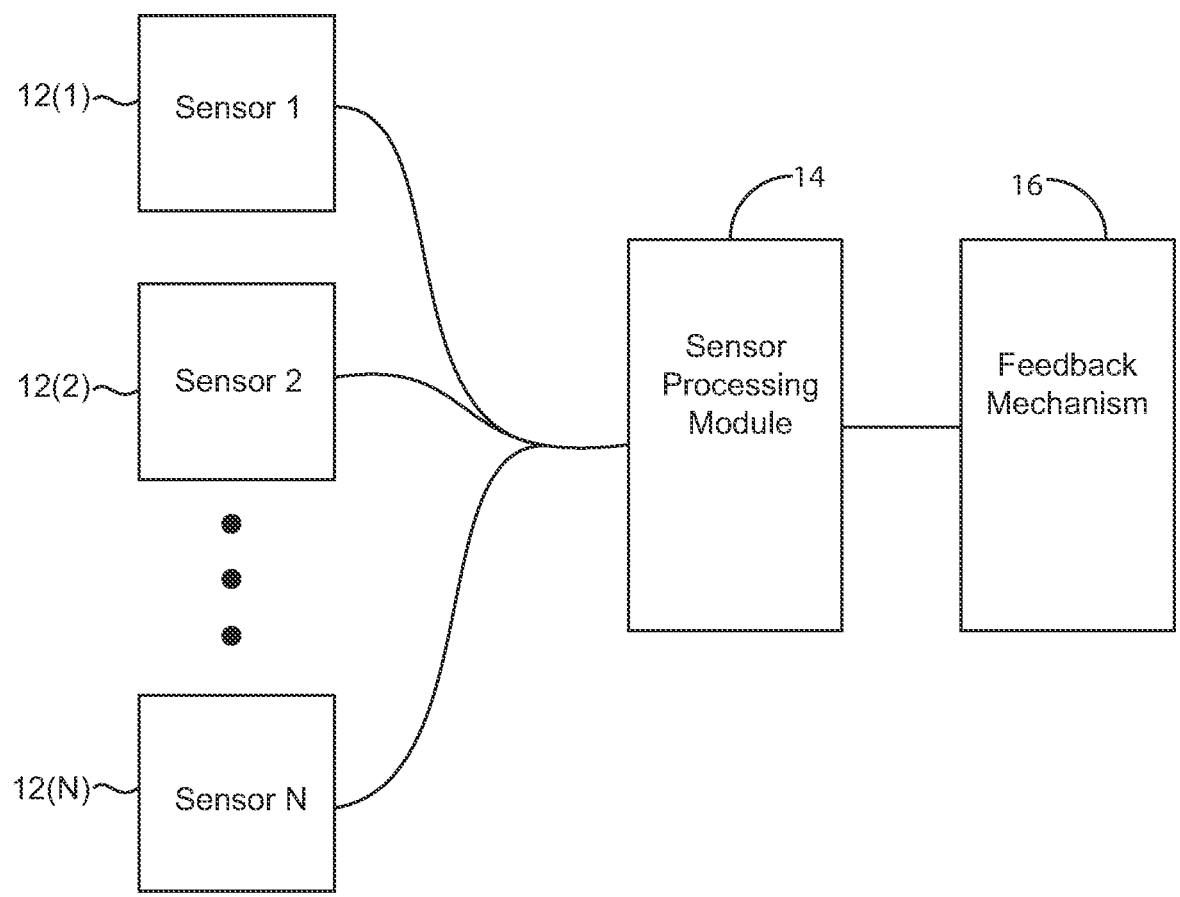
FIG. 1 is a block diagram of a stress management system.
Figure 3:
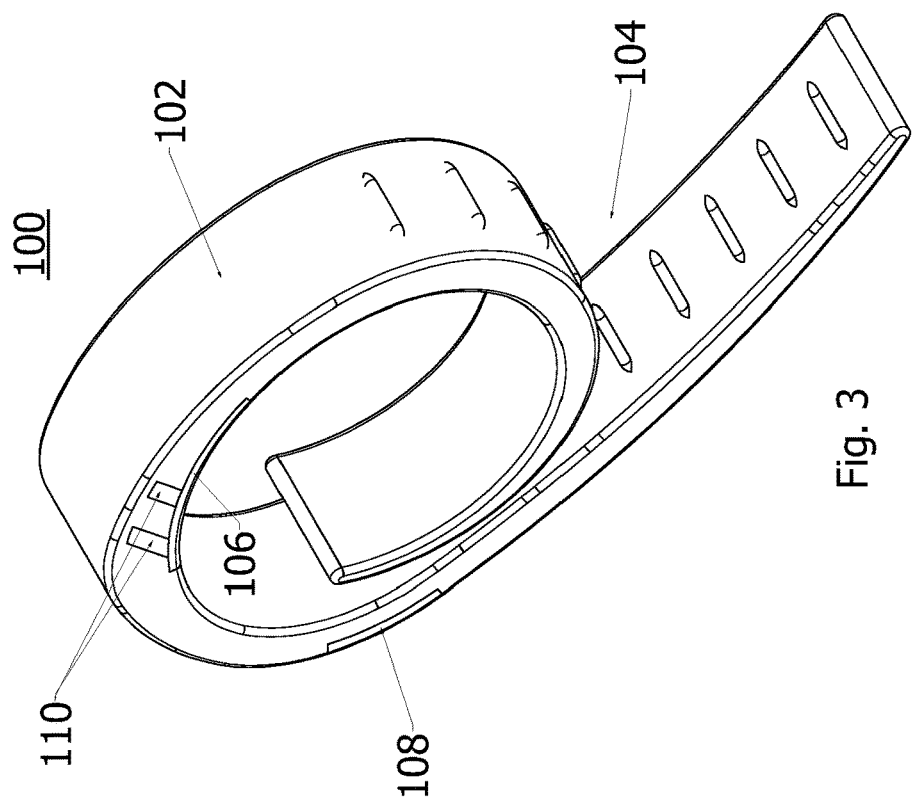
FIG. 3 is another perspective view of the biometric monitoring device of FIG. 2.
Figure 2:
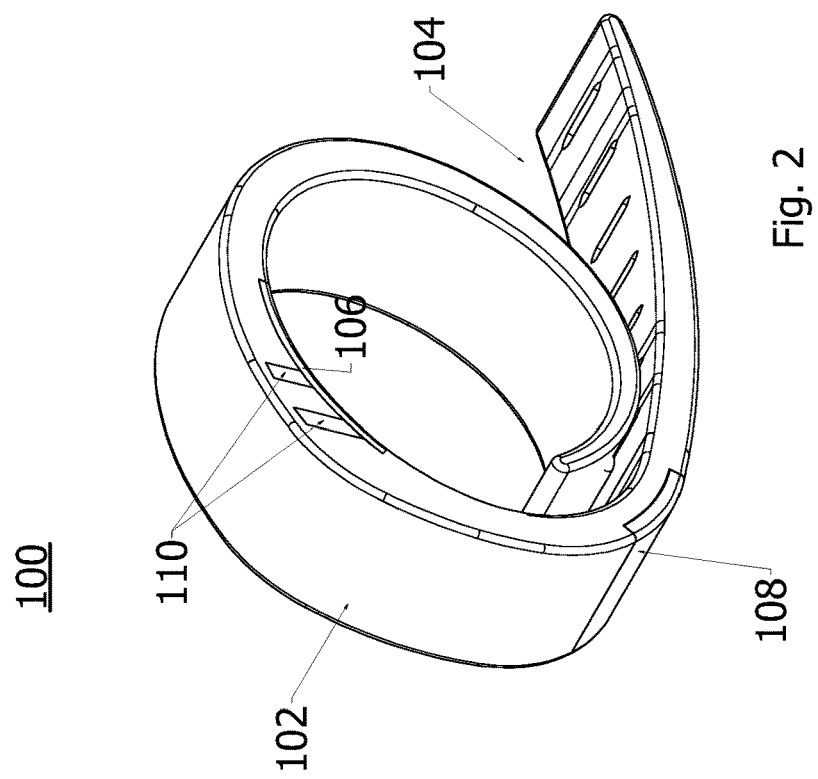
FIG. 2 is a perspective view of a biometric monitoring device.

FIG. 1 is a schematic block diagram of a stress management system 10. The system 10 includes a plurality of sensors 12(1)-12(N), a sensor processing module 14 and a feedback mechanism 16. Each of the sensors 12 are positioned to sense a signal from a user and provide the corresponding signal to the sensor processing module 14. The signal, in one embodiment, is an indication of electrical activity (e.g., electrical potential) at selected positions on the user's skin. In one embodiment, a first sensor 12 can be positioned to face a wrist of the user and a second sensor 12 can be positioned opposite the first sensor 12 for accessible contact by the hand opposite the wrist that is attached to the sensor 12. In further embodiments, sensors 12 can be coupled with other portions of the body. In still further embodiments, any number of sensors 12 can be provided in order to increase a quantity and/or quality of signals desired for measurement. In any event, the sensors 12 are positioned, in one embodiment, to sense electrical activity of the heart of the user. In further embodiments, other biometric values of the user can be measured independently, or concurrently therewith, the electrical activity.

Regardless of the number of sensors used, the sensors 12 can provide signals to the sensor processing module 14. The sensor processing module 14 interprets the signals received from the sensor 12 and calculates a biometric value associated with the user. In one embodiment, the value calculated is heart rate variability of the user with the sensor processing module validating data received from the sensors 12. Based on the biometric value, the feedback mechanism 16 provides feedback (e.g., biofeedback) to the user. In one example, as heart rate variability changes as measured at a selected interval, the feedback mechanism 16 can alter a feedback signal provided to the user as desired. In the event the heart rate variability of a user increases, the feedback mechanism can deliver a first signal to the user. In the event the heart rate variability decreases, the feedback mechanism 16 can provide a second, different signal to the user. In addition, if the heart rate variability stays approximately the same, the feedback mechanism 16 can provide a third signal, different from the first and second signals, to the user. The heart rate variability, in one embodiment, is measured in the time domain as the time interval between heartbeats.

In one embodiment, the system 10 can be implemented using a single wearable device, such as a wrist band. In this embodiment, a first sensor 12 can be positioned to contact a wrist of the user and a second sensor 12 can be positioned such that a user can place a finger or other contact point against the second sensor 12 so that electrical activity can be measured. The sensor processing module 14 can be provided within the wearable device, positioned remote from the wearable device or otherwise include processing functions distributed both within the wearable device and on a device remotely coupled therewith. In like manner, the feedback mechanism 16 can be coupled directly with the wearable device or remotely coupled with the wearable device.

FIGS. 2-7 illustrate one example embodiment of a biometric monitoring device 100 that is configured to measure biometric data of a user. In one embodiment, the device 100 can include each of the elements of system 10 illustrated in FIG. 1. In other embodiments, the system 10 can include other elements that function with the device 100 so as to provide stress management for a user. Regardless of the particular implementation, biofeedback from the biometric monitoring device 100 can be used by the user to monitor his/her own health or performance in real time. As illustrated, the device 100 generally comprises a band 102 configured to be worn about a wrist of the user. The band 102 includes an adjustment mechanism 104 (e.g., cooperative magnetic elements) for adjusting a circumference of the band 102. A user can thus select, using adjustment mechanism 104, a particular size for positioning band 102 about the user's wrist.

A first sensor 106 (e.g., an electrode facing the wrist of the user) is positioned about the band 102 at a first position, whereas a second sensor 108 (e.g., an electrode facing away from the wrist of the user) is positioned about the band 102 at a second position. A visual indicator 110 can further be positioned on the band 102 to provide visual signals to the user. The sensors 106 and 108 are configured to be activated by a button integral with the sensor 108. The button, in general, is a mechanism through which a user input or activation signal may be received or recognized by the biometric monitoring device 100 in order to initiate heart rate measurement via the sensors 106, 108. The sensors 106, 108 are any type of sensor that suits the needs of the user. The sensors 106, 108 are coupled directly to the user, worn on the clothing or skin of user, carried by user, or placed in proximity to user depending on the type of sensor. Various combinations of sensors can provide more accurate reading on stress changes as desired. One or more translucent windows 110 can further be positioned about the band 102 to transmit light from one or more indicators positioned with the band 102.

Figure 5:
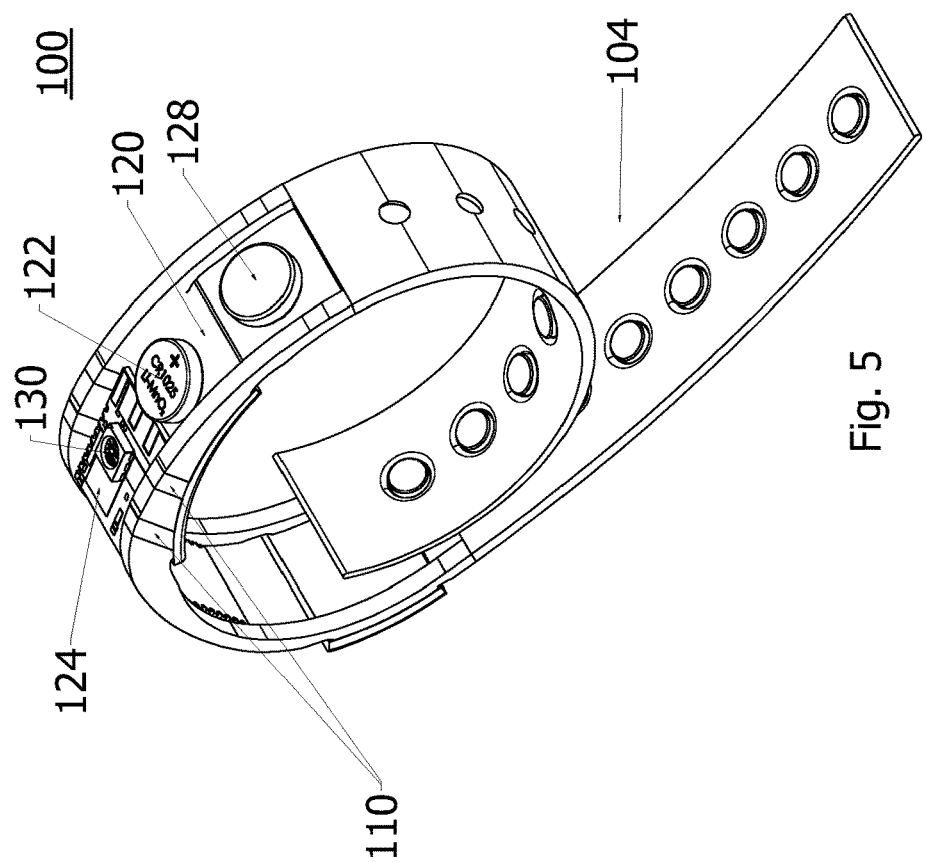
FIG. 5 is another perspective view of the biometric monitoring device of FIG. 2 with portions removed.
Figure 4:
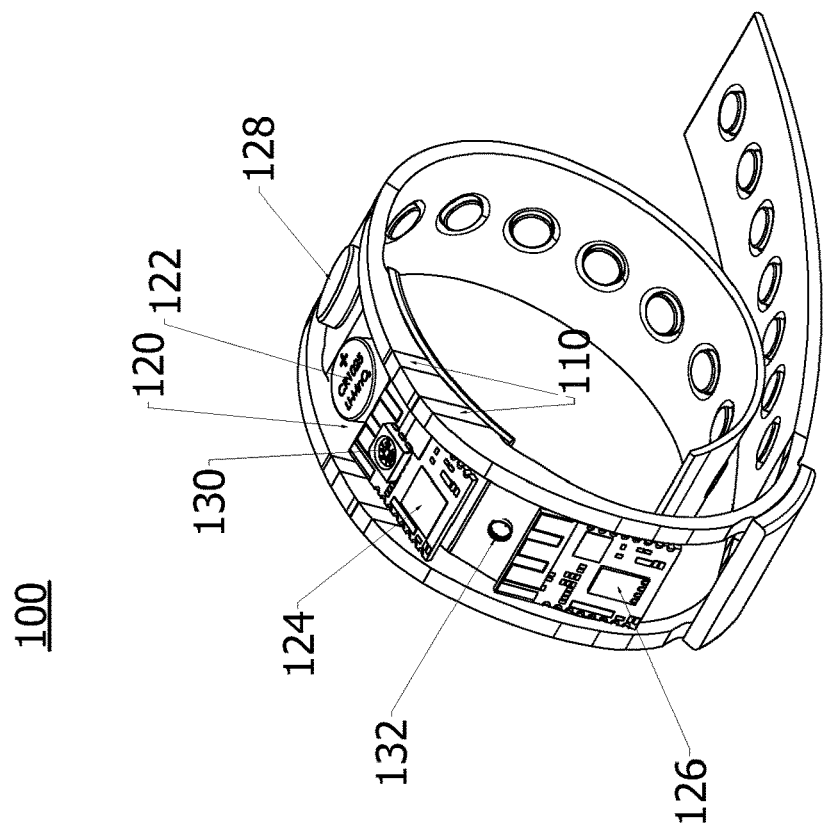
FIG. 4 is a perspective view of the biometric monitoring device of FIG. 2 with portions removed.

The biometric monitoring device 100, in one embodiment, is used to lower the user's heart rate by facilitating biofeedback through vibrations transmitted to the user. To this end, biometric monitoring device 100 can operate as a meditation and relaxation tool for users. In particular, a vibration pattern of frequency, duration and magnitude can be selected to encourage a desired behavior. As illustrated in FIGS. 4 and 5, the biometric monitoring device 100 comprises an electronic cavity 120. Within the cavity 120, at least one battery 122, a central computer 124, a biometric value calculator 126 and a biofeedback indicator 128 are positioned. The biofeedback indicator 128 in one embodiment includes a vibration motor operating as a feedback mechanism. The central computer 124 can include a processor and memory mounted to a printed circuit board as illustrated. The processor of the central computer 124 can be used to activate or trigger the biofeedback indicator 128 according to the biometric value calculated that is sensed by the sensors 106, 108 and evaluated by the biometric value calculator 126. The memory can store computer-executable instructions for controlling the processor of the central computer 124.

The biofeedback provided to the user by the biofeedback indicator 128 enables the user to self-regulate the user's activity and behavior in order to improve the user's performance or health. Accordingly, the biometric monitoring device 100 provides personal biofeedback customized for the user. The biofeedback allows the user to learn about the user's personal physiological state and physiological responses. By continuously monitoring one or more biometric value, the user can respond to the data received and modify behavior or activity to improve health and performance. By utilizing the biometric monitoring device 100, the user can train his/her brain to reduce anxiety, stress, and the severity of ADD/ADHD.

The biometric calculator 126 processes biometric data measured by the sensors 106, 108 and produces biofeedback correlating to the processed biometric data. The biometric monitoring device 100 thereby provides biofeedback by sensing and reporting a biometric value measured by the sensors 106, 108 to the user in real time. In one embodiment, real time is less than 1 second, less than 750 milliseconds, less than 500 milliseconds or any other value to provide immediate feedback to the user. The biometric monitoring device 100 is configured to provide user feedback, through the biofeedback indicator 128, with reference to the collected biometric data such as heart rate variability. The biometric monitoring device 100 emits vibrations based on the user's changing heart rate variability.

A visual indicator 130 (e.g., a light emitting diode) can be provided within the electronic cavity 120 and configured to emit different colors based on when the user is supposed to inhale and exhale for deep breathing relaxation techniques. The user is capable of changing the breathing intervals. The breathing intervals can be adjusted with the same button 108 to turn on the visual indicator 130. In the embodiment illustrated, visual indicator 130 is communicatively coupled with the central computer 124 and configured to change color in response to signals received from the central computer 124. The electrical cavity 120 can further include an inductive coil 132 configured to generate current therein in response to a magnetic field so as to provide a direct current to charge battery 122.

FIGS. 6 and 7 illustrate an exemplary charging stand 150 used to provide power to the device 100. The stand 150 defines a port 152 (e.g., a USB-C port or other similar port) to receive power from an outlet. Circuitry 154 (schematically illustrated) within the stand 150 provides power to a coil 156 (schematically illustrated) configured to generate current within the inductive coil 132. This current can then be used to charge the battery 122.

During operation, heart rate variability of the user can be measured by calculating electric potential between electrode 106 and electrode 108. In sensing the electric potential, the biometric calculator 126 can calculate a time between heart beats as the heart rate variability. Calculations of the heart rate variability can be compared with other calculations at different times to determine a feedback signal to provide to the user through biofeedback indicator 128. Collected biometric data can link to an external app or website database for storage. For example, a smart phone app and website database link up to the biometric monitoring device 100 (e.g., through a wireless communication module on central computer 124) can obtain and record all data for use by the user. Until the data is linked and downloaded, it will be stored in the biometric monitoring device 100. Also, the heart rate patterns and all past data are accessible.

Figure 8:
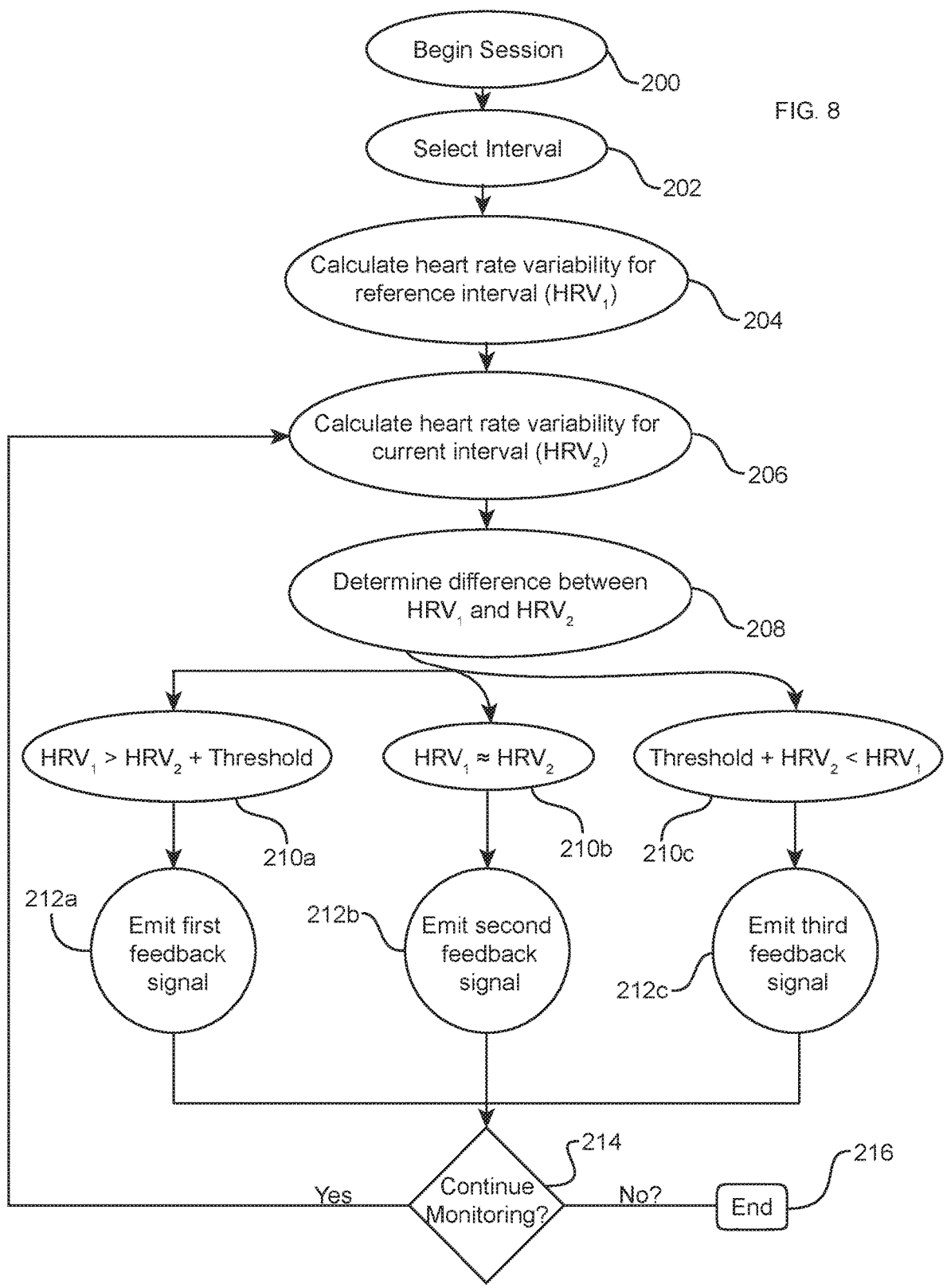
FIG. 8 is a flow diagram of a method of providing biofeedback in a stress management system.

FIG. 8 depicts a flow diagram of a method of operation of biometric monitoring device 100. The method is initiated using biometric monitoring device 100 with heart rate variability measuring function by actuating the button 108 and thereby beginning a feedback session at step 200. The sensors 106, 108 are activated in response to the activation signal sent by the button 108. The collected data is transmitted to the biometric calculator 126. In one embodiment, the central computer 124 in real-time evaluates if there is a change in the heart rate variability compared with a previous calculation of a past interval. The central computer 124 is configured to receive biometric data obtained in response to the activation signal from the sensors 106, 108 and compare the biometric data with a reference biometric data stored in memory. For example, the comparison can be performed with respect to a previous heart rate variability calculation over a prior interval.

The biofeedback indicator 128 is arranged inside the electronic cavity 120 of the biometric monitoring device 100 (See FIG. 1). Biofeedback vibrations can be given in different increments of time as desired and as a function of heart rate variability sensed from the user. The vibrations can differ in both duration and magnitude. For example, a short, sharp and abrupt vibration is emitted if the heart rate variability goes up, and a longer, smooth and gentle vibration is emitted if the heart rate variability goes down, and a steady calm vibration or none at all given for that interval if there is no change in the measured heart rate. Concurrently, the visual indicator 130 displays a light based on when the user is supposed to breathe in and out, the light continuously changing color on a set interval of time. The user is capable of changing the breathing intervals. The breathing intervals can be adjusted with the same button 100 to turn on the biofeedback indicator 128. The user can adjust the breathing intervals with the smart phone app as well.

After step 200, the method proceeds to step 202 wherein an interval is selected. The interval can be selected based upon a number of different factors. For example, if the user is focused on relaxing, an example interval of 15 to 30 seconds can be selected in order to increase the focus of the relaxation session. In other instances, a longer interval such as anywhere from 60 to 90 seconds can be selected so as to not readily disturb the user in the event the user is performing another task. In an alternative embodiment, the interval can be dynamic, for example, gradually increasing or gradually decreasing as desired. In one embodiment, the interval can be selected from a remote system (e.g., a phone paired with device 100). Next, at step 204, the heart rate variability is calculated during a reference interval ($HRV_1$). In one embodiment, this calculation involves a single sample. In other embodiments, measurements can be obtained over the entire interval, part of the interval or otherwise. These measurements can be used to calculate a median interval or average of the intervals as calculated.

Next, at step 206, the heart rate variability is further calculated for a current interval ($HRV_2$). Given the two values, a difference between the heart rate variability for a reference interval ($HRV_1$) and the heart rate variability of the current interval ($HRV_2$) can be determined. In one embodiment, the change in heart rate variability can be compared in reference to a particular threshold. Based on this difference, the method can proceed to one of three feedback options 210. For example, if the heart rate variability has decreased an amount above a particular threshold, the method proceeds to step 210A. If the heart rate variability remains approximately unchanged (e.g., within the threshold), the method proceeds to step 210B. Alternatively, if the heart rate variability has increased above the threshold, the method proceeds to step 210C.

Depending upon which step the method executes, a first, second or third feedback signal is emitted, as noted by signals 212A, 212B and 212C. The different feedback signals can be emitted so as to indicate change in stress levels. In one embodiment, the duration, frequency and magnitude of a vibration pattern is selected as the signal so as to alter behavior of the user in the session. For example, if the heart rate variability has increased, a long, calming and massaging vibration can be emitted. Alternatively, if the heart rate variability has decreased, a short and abrupt vibration can be emitted. If the heart rate variability has remained constant (e.g., within a threshold), a shorter, calming and massaging vibration is emitted that is different from either of the other signals emitted. After the feedback signal is emitted, the method continues to step 214, where it is determined whether monitoring should continue. A number of different factors can be used at this point to determine if monitoring should be continued or the method should proceed to end at step 216. For example, if a user's heart rate variability has increased for a specified number of intervals (e.g., 2, 3, 4, 5, 6 or more), the method can end. If the session is to continue, the method proceeds to step 206, wherein heart rate variability for a current interval is calculated. In this instance, the previous heart rate variability value can become the reference value ($HRV_1$) or the reference value can remain unchanged for comparison purposes.

The foregoing description of the preferred embodiment of the present invention has been presented for the purpose of illustration and description. It is not intended to be exhaustive or to limit the invention to the precise form disclosed. Many modifications and variations are possible in light of the above teachings. It is intended that the scope of the present invention not be limited by this detailed descriptions but by the claims and the equivalents to the claims appended hereto.

Various embodiments of the invention have been described above for purposes of illustrating the details thereof and to enable one of ordinary skill in the art to make and use the invention. The details and features of the disclosed embodiment[s] are not intended to be limiting, as many variations and modifications will be readily apparent to those of skill in the art. Accordingly, the scope of the present disclosure is intended to be interpreted broadly and to include all variations and modifications coming within the scope and spirit of the appended claims and their legal equivalents.

The invention claimed is:

1. A wearable device for monitoring biometric data of a user, the device comprising:

a plurality of sensors configured to collect biometric data from the user;

at least one processor having memory and instructions, the at least one processor being coupled to the plurality of sensors and configured to receive the biometric data from the plurality of sensors;

a first indicator coupled to the at least one processor and activated by a control signal from the at least one processor, and the instructions, when executed by the at least one processor while the device is being worn by the user, causing the at least one processor to:

receive first biometric data from the plurality of sensors throughout a first time interval;
calculate a first heart rate variability (HRV) value from all the received first biometric data;
receive second biometric data from the plurality of sensors throughout a second time interval immediately following the first time interval;
calculate a second HRV value from all the received second biometric data;
compare the second HRV value to the first HRV value and when a result of the comparison is that the second HRV value is increased over the first HRV value by a threshold amount, activate the first indicator to indicate an increase of the second HRV value from the first HRV value;
receive third biometric data from the plurality of sensors throughout a third time interval immediately following the second time interval;
calculate a third HRV value from all the received third biometric data;
compare the third HRV value to the second HRV value and when a result of the comparison is that the third HRV value is increased over the second HRV value by the threshold amount, activate the first indicator to indicate an increase of the third HRV value from the second HRV value;
consider the third HRV value to be a reference HRV value and the third time interval to be a reference time interval;
after receiving the third biometric data, receive new biometric data from the plurality of sensors throughout a new time interval immediately following the reference time interval;
calculate a new HRV value from all the received new biometric data;
compare the new HRV value to the reference HRV value and when the result of the comparison is that the new HRV value is increased over the reference HRV value by the threshold amount, activate the first indicator to indicate an increase of the new HRV value from the reference HRV value;
select the new HRV value as the reference HRV value and the new time interval as the reference time interval;
repeat the receiving of new biometric data, the calculating of a new HRV value, and the comparing of the new HRV value to the reference HRV value; and
discontinue repeating the receiving of new biometric data, the calculating of a new HRV value, and the comparing of the new HRV value to the reference HRV value after the new HRV value has increased for a specified number of intervals.

2. The wearable device of claim 1, further comprising a button coupled to the plurality of sensors, the button providing an activation signal to the plurality of sensors when the user actuates the button.

3. The wearable device of claim 1, wherein to indicate an increase of HRV value from the first HRV value or from the second HRV value, the instructions cause the at least one processor to activate the first indicator according to a first pattern.

4. The wearable device of claim 3, wherein the first indicator includes a haptic indicator and the first pattern includes a first vibration pattern of a selected frequency, duration and magnitude.

5. The wearable device of claim 3, further comprising a second indicator coupled to the at least one processor and activated by a control signal from the at least one processor, and the instructions cause the at least one processor to activate the second indicator to indicate a desired breathing pattern to the user.

6. The wearable device of claim 5, wherein the first indicator includes a haptic indicator, the first pattern includes a first vibration pattern of a selected frequency, duration and magnitude, and the second indicator includes a visual indicator.

7. The wearable device of claim 6, wherein the visual indicator is configured to emit a plurality of colors and the instructions cause the at least one processor to activate the visual indicator to emit a first color indicating that the user is supposed to inhale and to emit a second color indicating that the user is supposed to exhale.

8. The wearable device of claim 1, the instructions further causing the at least one processor to:
when the result of the comparison is that the second HRV value is less than the first HRV value by the threshold amount, activate the first indicator to indicate a decrease of the second HRV value from the first HRV value; and
when the result of the comparison is that the third HRV value is less than the second HRV value by the threshold amount, activate the first indicator to indicate a decrease of in the third HRV value from the second HRV value.

9. The wearable device of claim 1, wherein the first indicator is a visual indicator.

10. A method comprising:
providing a user with a wearable device comprising a processor, a plurality of sensors and a first indicator;
receiving, by the processor, an indication of initiation of a stress management session;
receiving, by the processor, first biometric data from the plurality of sensors throughout a first time interval;
calculating, by the processor, a first HRV value from all the received first biometric data;
receiving, by the processor, second biometric data from the plurality of sensors throughout a second time interval immediately following the first time interval;
calculating, by the processor, a second HRV value from all the received second data;
comparing, by the processor, the second HRV value to the first HRV value and when a result of the comparison is that the second HRV value is increased over the first HRV value by a threshold amount, activating, by the processor, the first indicator to indicate an increase of the second HRV value from the first HRV value;
receiving, by the processor, third biometric data from the plurality of sensors throughout a third time interval immediately following the second time interval;
calculating, by the processor, a third HRV value from all the received third biometric data;
comparing, by the processor, the third HRV value to the second HRV value and when a result of the comparison is that the third HRV value is increased over the second HRV value by the threshold amount, activating, by the processor, the first indicator to indicate an increase of the third HRV value from the second HRV value;
considering, by the processor, the third HRV value to be a reference HRV value and the third time interval to be a reference time interval;
after receiving the third biometric data, receiving, by the processor, new biometric data from the plurality of sensors throughout a new time interval immediately following the reference time interval;

calculating, by the processor, a new HRV value from all the received new biometric data;

comparing, by the processor, the new HRV value to the reference HRV value and when the result of the comparison is that the new HRV value is increased over the reference HRV value by the threshold amount, activating, by the processor, the first indicator to indicate an increase of the new HRV value from the reference HRV value;

selecting, by the processor, the new HRV value as the reference HRV value and the new time interval as the reference time interval;

repeating, by the processor, the receiving of new biometric data, the calculating of a new HRV value, and the comparing of the new HRV value to the reference HRV value; and discontinuing, by the processor, the repeating the receiving of new biometric data, the calculating of a new HRV value, and the comparing of the new HRV value to the reference HRV value after the new HRV value has increased for a specified number of intervals.

11. The method of claim 10, wherein to indicate an increase of HRV value from the first HRV value or from the second HRV value, the instructions cause the processor to activate the first indicator according to a first pattern.

12. The method of claim 11, wherein the wearable device further comprises a visual indicator, and wherein the first indicator includes a haptic indicator, the first pattern includes a first vibration pattern of a selected frequency, duration and magnitude, the method further comprising:
activating, by the processor, the visual indicator to indicate a desired breathing pattern to the user.

13. The method of claim 12, wherein the visual indicator is configured to emit a plurality of colors, the method further comprising:
causing, by the processor, the visual indicator to emit a first color indicating that the user is supposed to inhale, and to emit a second color indicating that the user is supposed to exhale.

14. The method of claim 10 further comprising:
when the result of the comparison is that the second HRV value is less than the first HRV value by a threshold amount, activating, by the processor, the first indicator according to a second pattern to indicate a decrease of the second HRV value from the first HRV value; and
when the result of the comparison is that the third HRV value is less than the second HRV value by the threshold amount, activating, by the processor, the first indicator according to the second pattern to indicate a decrease of the third HRV value from the second HRV value.

15. The method of claim 10 further comprising:
when the result of the comparison is that the second HRV value is within the threshold amount from the first HRV value, activating, by the processor, the first indicator according to a third pattern to indicate no change in the second HRV value from the first HRV value; and
when the result of the comparison is that the third HRV value is within the threshold amount from the second HRV value, activating, by the processor, the first indicator according to the third pattern to indicate no change in the third HRV value from the second HRV value.

16. The method of claim 10, wherein the first indicator is a visual indicator.

* * * * *